United States Patent [19]
Andrews et al.

[11] Patent Number: 5,767,414
[45] Date of Patent: Jun. 16, 1998

[54] AUTOMATICALLY ALIGNING TOOL FOR UNIFORMLY APPLYING A CONTROLLED FORCE TO AN OBJECT

[75] Inventors: Thomas Andrews, Creedmoor; Mohsen Hajirahim, Cary; Bill Palcisko, Durham, all of N.C.

[73] Assignee: Mitsubishi Semiconductor America, Inc., Durham, N.C.

[21] Appl. No.: 810,787

[22] Filed: Mar. 5, 1997

[51] Int. Cl.$^6$ .................................................. G01N 3/24
[52] U.S. Cl. ................................................................ 73/842
[58] Field of Search .......................... 73/788, 824, 842, 73/843, 846

[56] References Cited

U.S. PATENT DOCUMENTS

| | | |
|---|---|---|
| 102,577 | 5/1870 | Newell et al. . |
| 824,724 | 7/1906 | Keays . |
| 1,015,171 | 1/1912 | Goble . |
| 1,055,959 | 3/1913 | Whitehead . |
| 1,558,742 | 10/1925 | Maszczyk . |
| 2,024,112 | 12/1935 | Phillis . |
| 2,744,430 | 5/1956 | McLaughlin et al. . |
| 3,071,368 | 1/1963 | Harding . |
| 3,174,333 | 3/1965 | Behre . |
| 3,491,643 | 1/1970 | Meinholdt . |
| 3,535,914 | 10/1970 | Veith et al. ........................ 73/843 X |
| 3,661,013 | 5/1972 | Wilcox ............................... 73/842 X |
| 3,866,897 | 2/1975 | Whalen, Jr. . |
| 4,343,190 | 8/1982 | Danko et al. ........................... 73/846 |
| 4,346,602 | 8/1982 | Gould et al. . |
| 4,445,387 | 5/1984 | Hall et al. . |
| 4,957,004 | 9/1990 | McKinlay et al. . |

FOREIGN PATENT DOCUMENTS

| | | |
|---|---|---|
| 61-259138 | 11/1986 | Japan . |
| 1534371A | 4/1988 | U.S.S.R. . |

*Primary Examiner*—Elizabeth L. Dougherty
*Attorney, Agent, or Firm*—McDemott, Will & Emery

[57] ABSTRACT

An apparatus for applying a uniform load to an object includes a load application element supported to be rotatable about a first axis and movable relative to the object along a second axis to obtain an initial contact sufficient to cause any needed rotation of the load application element until an alignment is obtained between the load application element and a load receiving surface of the object. Further movement of the load application element relative to the object results in a uniformly applied load or the test object.

13 Claims, 3 Drawing Sheets

AUTOMATICALLY ALIGNING TOOL FOR UNIFORMLY APPLYING A CONTROLLED FORCE TO AN OBJECT

TECHNICAL FIELD OF THE INVENTION

This invention relates to a tool for automatically aligning a force-applying element to a workpiece supported to a base, and more particularly to a tool in which an element for applying a measurable shear force automatically aligns itself to an initially contacted portion of the workpiece for application of a uniform force thereto.

BACKGROUND OF THE RELATED ART

In the manufacture of semiconductor devices it is quite common to employ an adhesive material, e.g., an epoxy glue, to bond an element such as a die to another element such as a die-pad. Such a structure may also be employed in equipment for manufacturing other components or structures, and the amount of shear loading tolerated by the bond between an exemplary die and a die pad supporting the same may be a significant manufacturing parameter. It therefore becomes important to uniformly apply a controlled measurable shear load to a bonded element to determine the shear strength of the mounting bond.

As will be readily appreciated, if a load element is forcibly applied to the test element, and there is any misalignment between them, the applied load may tend to be concentrated at the initial location of contact and this may skew the conduct of the interacting elements as well as the measured test results. It is therefore important to obtain an operational contact which will ensure uniform application of force to the test element during the substantive load-applying test procedure.

There are other circumstances in conventional testing methods where misalignment is encountered. Various solutions to address such problems are known but are usually specific to the particular problem being solved.

U.S. Pat. No. 4,445,387, to Hall et al. titled "Compression Shear Test Jig", teaches a test jig structure for determining the internal shear strength of the weakest plane of a wood fiber or particle panel product. It includes upper and lower loading heads provided with respective opposed sample engaging faces disposed at a 45° angle to the direction of application of the primary force applied to generate shear loading in a sample. The upper loading head includes a pivoted cap resting on a spherical ball. The shear-generating force is obtained by a downward load on the pivoted cap which rests on an upper portion of the spherical ball and aligns as needed without forcing the upper loading head to significantly alter its orientation under the applied load. The sample is thus sandwiched between the upper and lower heads and the ball-adjusted force is then applied to and through the upper head.

U.S. Pat. No. 4,957,004, to McKinlay et al., titled "Testing Apparatus", teaches a device for testing the adhesive strength of a bond between the liner and a medium in corrugated paper board. The corrugated paper board specimen is placed between two clamps, the top clamp being a plastic strip clipped to a tongue which allows alignment of the clamp parallel to the flutes of the corrugated paper board. The top clamp forcibly pulls the top board free of the glue holding the corrugation portion in place, and this provides information on the strength of the bond at the corrugations.

U.S. Pat. No. 3,174,333, to Behre, titled "Apparatus for Determining the Resistance to Shear Effect in Plane Fabrics and Similar Materials", teaches an apparatus which includes two clamps respectively assembled to top and bottom portions of a cloth specimen. The original cloth specimen is rectangular, the upper clamp is pivotably supported at a location distant from its center, and the load on the fabric is provided by gravity acting on the lower clamp and tends to distort the specimen shape to rupture. This is an instance where misalignment is deliberately generated in a test.

These and other known devices provide a certain amount of alignment correction or control between components of the test equipment. However, they do not provide a solution to the problem of how to ensure that a uniform shear force is provided by a tool to an affixed sample so that there is no non-uniform loading and/or shear force application to the sample during a test.

The present invention is intended to address this long-felt need and does so in a very simple and cost-effective manner such that any initial misalignment between a load-applying element and the loaded object is automatically overcome prior to substantive test loading.

DISCLOSURE OF THE INVENTION

Accordingly, it is a principal object of this invention to provide an apparatus in which a tool movable to apply a controlled and measurable force automatically aligns to an affixed sample object to ensure uniform force application thereto.

It is another object of this invention to provide apparatus for moving a load-application element toward a fixed test object in such a manner that the load-applying element automatically aligns to the test object prior to substantive application of force.

It is yet another object of this invention to provide a method for determining the strength of a bond between a test specimen and a test bed, by applying to the specimen an automatically aligned uniform force in controlled and measurable manner.

Accordingly, there is provided in a preferred embodiment of this invention an apparatus for applying a uniform load to an object. This apparatus includes a loading element mounted to be freely rotatable about a first axis and having a load application surface rotatable at a first radius about the first axis. The apparatus also includes a first means for controllably moving the loading element along a second axis which is oriented perpendicular to the first axis. A second means is provided for holding the object, so that in a first phase of operation a load-receiving surface of the object is disposed to make contact with the load application surface of the moving loading element to rotate the loading element about the first axis as needed to align the load application surface into making uniform contact over a contact area of the load receiving surface. In a second phase of the operation, the uniform contact is maintained while further controlled movement of the loading element applies a uniform load to the object.

In another aspect of this invention there is provided an apparatus for determining the strength of a bond between a specimen and mounting element to which the specimen is bonded. This apparatus includes a loading element which is movable in translation along a first axis passing through the specimen and rotatable about a second axis oriented perpendicular to the first axis. The apparatus also includes means for moving the loading element and the specimen relative to each other along the second axis until contact between the loading element and the specimen causes a rotation of the loading element about the second axis sufficient to ensure uniform contact between the loading element and the specimen.

In yet another aspect of this invention, there is provided a method of applying a uniform force to a test specimen, comprising the steps of obtaining a contact between a rotatably mounted movable load application element and the test specimen sufficient to generate an alignment between mutually contacting surfaces of the load application element and the test specimen prior to substantive load application.

DETAILED DESCRIPTION OF THE PREFERRED EMBODIMENTS

Figure 1:
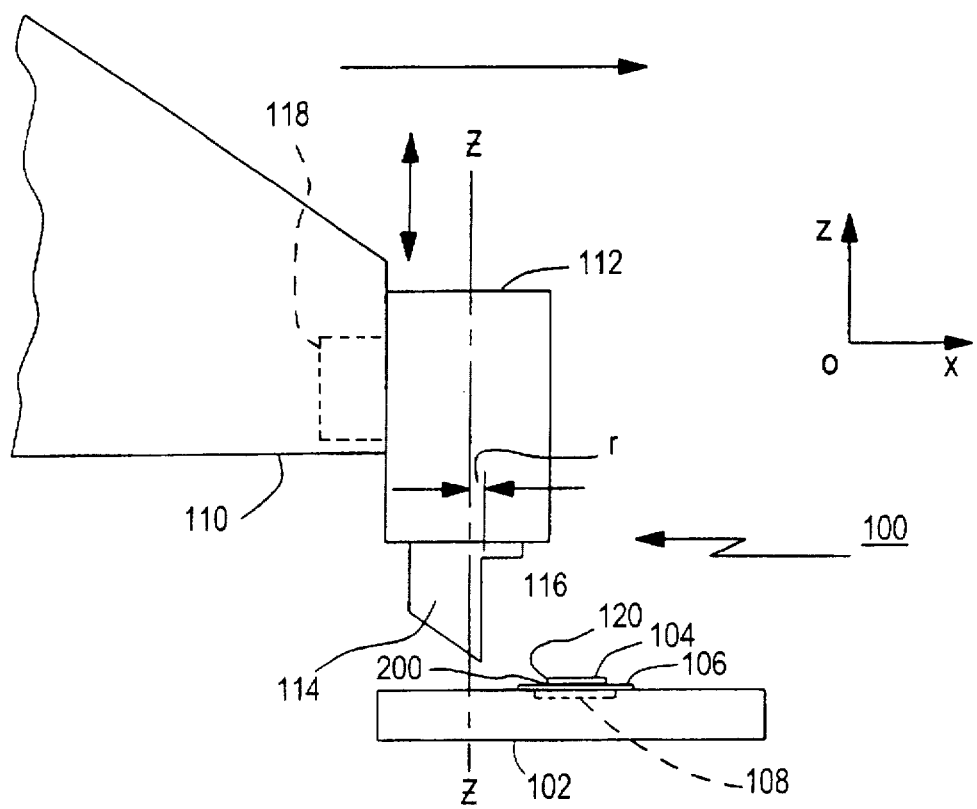
FIG. 1 is a side elevation view of the apparatus according to a preferred embodiment of this invention.

As best seen in FIG. 1, the apparatus 100 according to a preferred embodiment of this invention includes a base 102 having an upper surface on which may be mounted an object or test specimen 104 to which a carefully controlled and measured force is to be applied. In an exemplary application of such an apparatus, e.g., to determine the shear strength of a bond 200 between the test specimen 104 in the form of a die affixed with an epoxy resin to a die pad 106, the latter may be itself mounted in any known manner, e.g., with bolts, clamps, or the like to the upper surface of base 102. Also, as schematically illustrated in FIG. 1, a force-measuring element, e.g., a strain gauge 108 or the like, may be provided between the die pad 106 and base 102 so that a force applied to die 104, communicated via bond 200 through die pad 106, may be measured, perhaps as a function of time, by the known load-measuring element 108 and conventional recording apparatus (not shown). Since strain gauges, piezoelectric devices, and the like are commercially available in a great variety, and their uses are well-known, details of how they may be mounted and employed are not recited herein. Persons of ordinary skill in the art can be expected to know how to select and employ such devices to determine the time history of a load applied to die 104, possibly through destruction of the bond 200 between die 104 and die pad 106, for purposes of analysis.

The apparatus 100 also includes a load-application component 110 mounted so as to be movable relative to the test specimen, e.g., die 104, to apply a carefully controlled and measurable force thereto. The load-applying component 110, in the first preferred embodiment of the apparatus 100, includes a support head 112 provided with suitable low-friction bearings of known type (not shown) which support a load-applying element 114 rotatably about a vertical axis Z—Z located centrally of the bearings. Head 114 preferably has a flat, planar, vertical load-applying face 116 located at a radius "r" distant from axis Z—Z. Head 114 may be mounted to be movable up or down.

Figure 2:
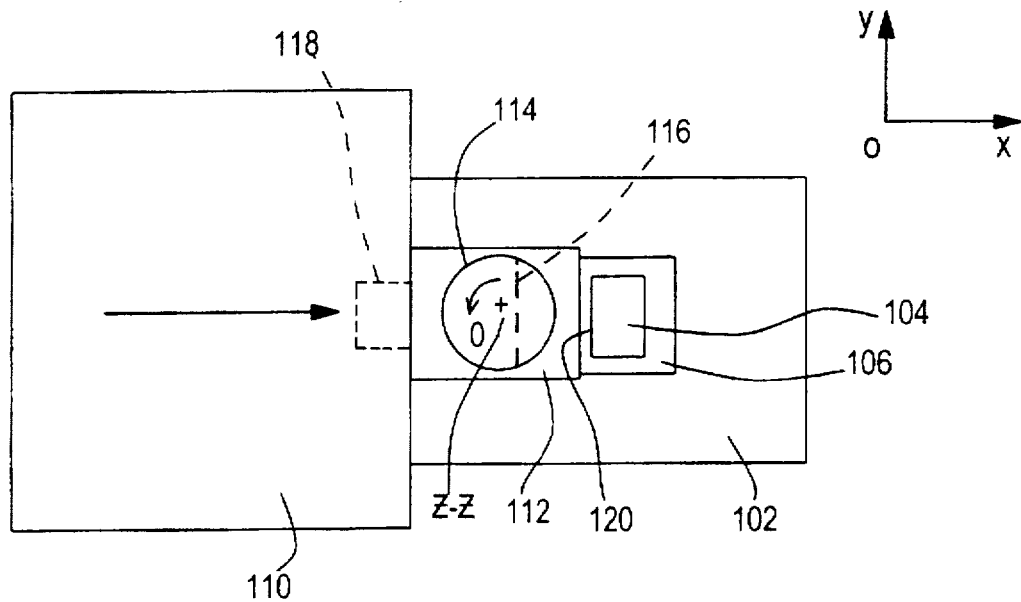
FIG. 2 is a plan view of the apparatus according to FIG. 1.

As will be appreciated by reference to FIGS. 1 and 2, there is provided with each a respective planar view of corresponding cartesian coordinate axis. Load-applying face 116 is parallel to the z-axis and perpendicular x-axis at all times in the preferred embodiment. As indicated in FIG. 2, the load-applying element 114, supported by low-friction bearings, is freely rotatable about axis Z—Z and may be easily rotated by the application of a force to load-applying face 116 thereof except when the force is directed exactly through the Z—Z axis. This is an important aspect of the invention and is utilized in operating the apparatus for its intended purpose as described more fully hereinbelow.

As noted earlier, a load-measuring element 108 may be provided in association with base 102. In the alternative, any suitable known type of load-measuring device or element 118 may be provided to work in cooperation with head 112 so that any direct or reaction force experienced by load-applying face 116 will generate a corresponding output in any suitable form as determined by the choice of load measurement element 118 and conventional ancillary equipment.

Instrumentation occasionally fails, and tests consequently do not always provide all of the desired data. One solution is to build in instrumentation redundancy to reduce the probability that all useful data will be lost. Furthermore, with redundant instrumentation it may be possible to average measurement values and, upon appropriate analysis, to derive more precise data than may be possible with a single instrument which may not be perfectly calibrated at the time of measurement.

Reference to FIG. 1 clarifies how the provision of two force-measuring devices such as 108 and 118 may provide both redundancy and the facility for obtaining ample data from a single test in which the load-applying surface 116 is utilized to apply a controlled force or load to test specimen such as die 104.

Reference to FIG. 2 shows how a perfectly oriented load-applying face 116 would be parallel to a correspondingly disposed load-receiving face 120 of the test specimen 104. If the load-applying face 116 is not rotatably supported as in the present invention, and if there is any non-parallelism between load-applying face 116 and the load-receiving face 120 of the test specimen 104, the initial point of contact would experience an uneven and much higher local stress than is intended and the test may consequently generate unusable data. The present invention very easily avoids such a situation, as best understood with reference to FIGS. 3–6 and the description that follows below.

Note that in FIGS. 3–6 the proportions of the various elements appear somewhat different from those in FIGS. 1 and 2. This is intended only to highlight certain geometric aspects of the invention.

Figure 3:
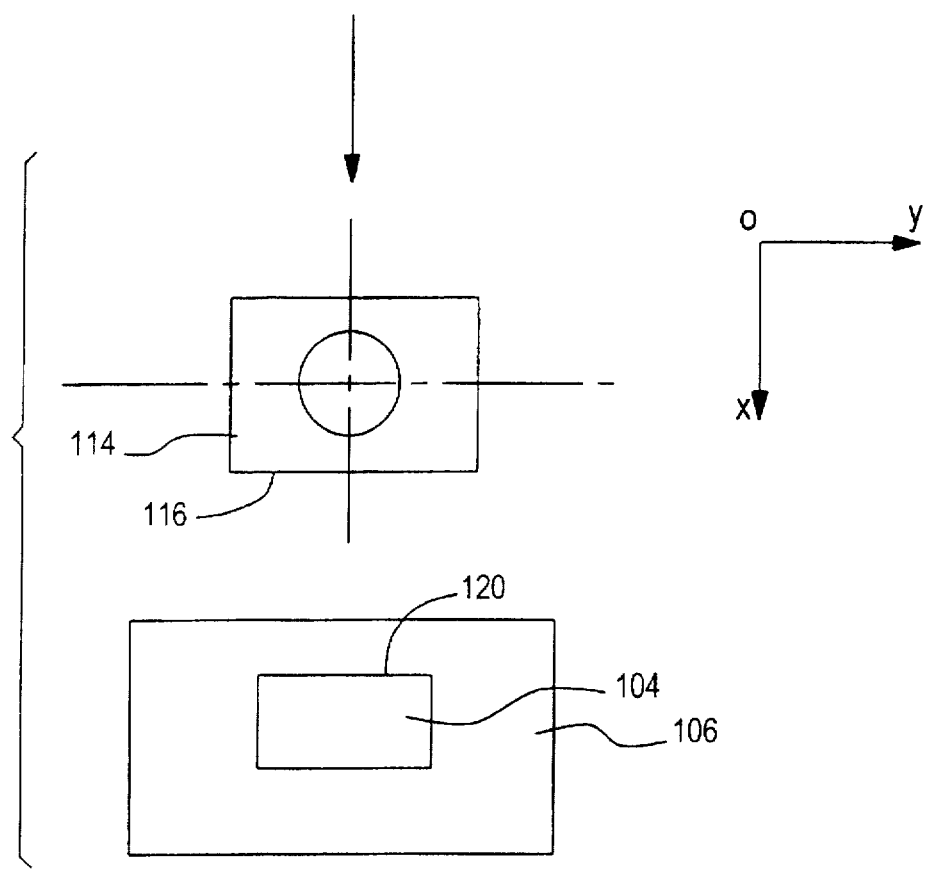
FIG. 3 is a schematic to illustrate an exemplary correct orientation between a force-applying element and a fixed specimen to be loaded thereby.

In FIG. 3 the load-applying face 116 is intended to be shown perfectly parallel to the load-receiving face 120 of specimen 104. If this circumstance can be obtained, relative movement between the test specimen and the load-applying head 114 should result in a uniform contact between load-applying face 116 and load-receiving face 120 so that there would not be any local concentration of stress. This may be considered the ideal situation.

Before proceeding further, it is important to appreciate that although the above discussion focuses on the first preferred embodiment in which the load-applying component 110 moves in both rotation and translation while specimen-supporting base 102 is held stationary, this is not necessary. In other words, with the provision of the rotatably supported load-applying head 114 the apparatus should work to produce exactly the same results even if the load-applying head were held stationary in translation and the specimen-supporting base 102 were moved towards it. Equally, if both the load-applying component 110 and specimen 104 were moved in translation towards each other, the end result should be no different. It is the relative movement between the load-applying face 116 and the load-receiving face 120, so that there is uniform contact between them prior to application of a substantive load, which is essential.

Figure 4:
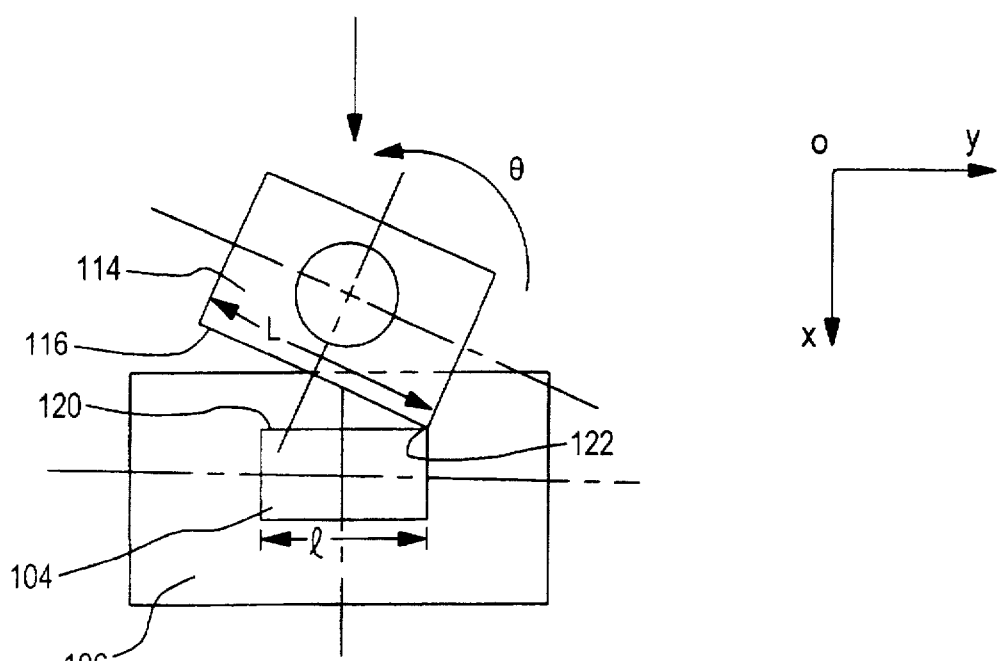
FIG. 4 is a schematic to illustrate an initial contact between a force-applying element according to the preferred embodiment and a misaligned test specimen.

FIG. 4 illustrates a situation in which there is an initial contact between load-applying face 116 and a misaligned load-receiving face 120 at an initial contact point 122. At this time, there is an angular separation, instead of perfect parallelism, between load-applying face 116 and load-receiving 120. However, further motion of load-applying element 114 toward specimen 104 will cause rotation, as indicated by the curved arrow, in the "θ" due to the interaction between rotatable load-applying head 114 and pressing thereon of specimen 104. In other words, in the schematic scenario shown in FIG. 4, the load-applying element 114 will rotate counterclockwise as it is moved closer to specimen 104. Eventually, load-applying element 114 will rotate sufficiently so that load-applying face 116 thereof is in uniform intimate contact with then parallel load-receiving face 120 of specimen 104. Subsequent motion of load-applying element 114 and specimen 104 towards each other will cause the load-applying element 114 to exert a uniform force on specimen 104 at their mutually contacted faces 116 and 120. Then, as described earlier, one or both of load-measuring elements 108 and 118 may be used to record the uniformly applied force, preferably as a function of time. When sufficient force is applied, the shear strength of the bond between specimen 104 and base 106 will be exceeded and there will be a shear rupture therebetween. The collected data may then be processed/interpreted in conventional manner to determine the shear strength of the bond. The quality of different epoxy adhesives, different treatments thereof, etc., may thus be analyzed.

Note that as indicated in FIG. 4 it is preferable to have the transverse dimension/size of load-applying face 116, i.e., "L" larger than the corresponding transverse dimension "l" of the load-receiving face 120 of specimen 104. This ensures that the relatively light preliminary contact between the load-applying element 114 and specimen 104, which results in whatever rotation is needed of load-applying element 114 about axis Z—Z, occurs so that load-applying face 116 extends beyond and outside of the load-receiving face 120 of specimen 104. This requires that "L" be greater than "l". If it were otherwise, i.e., if a portion of the load-receiving face 120 of specimen 104 extended beyond or outwardly of the load-applying face 116, specimen 104 would not receive the intended uniform force.

Figure 5:
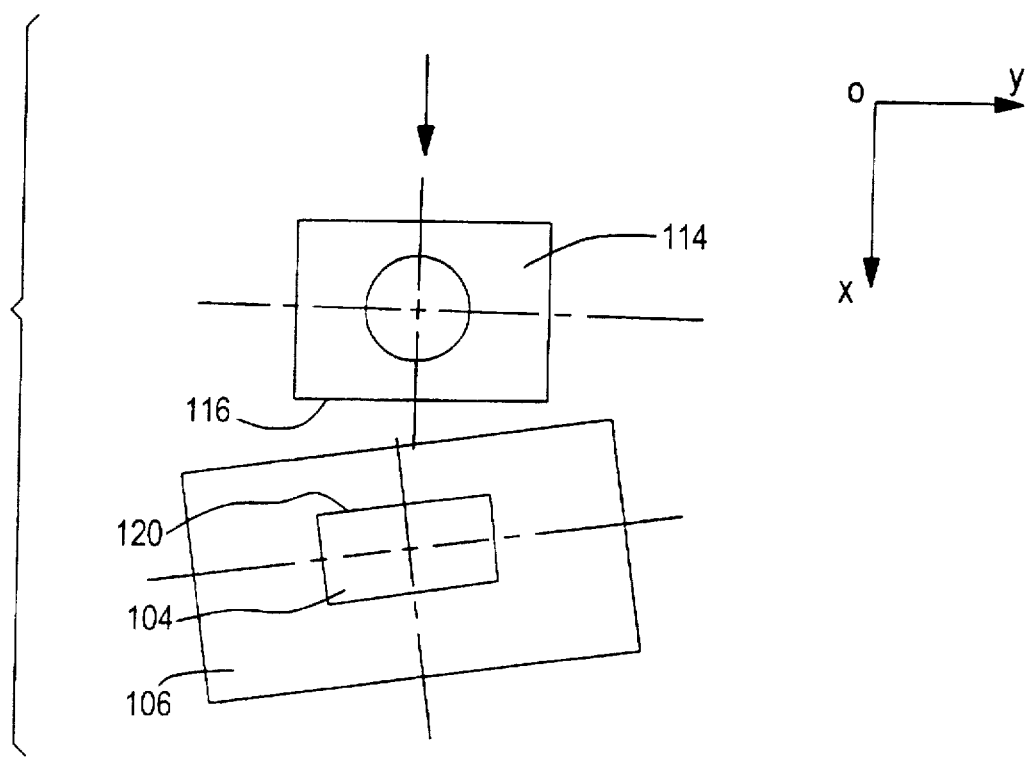
FIG. 5 is a schematic to illustrate a force-applying element and a specimen mounted in a misaligned manner.
Figure 6:
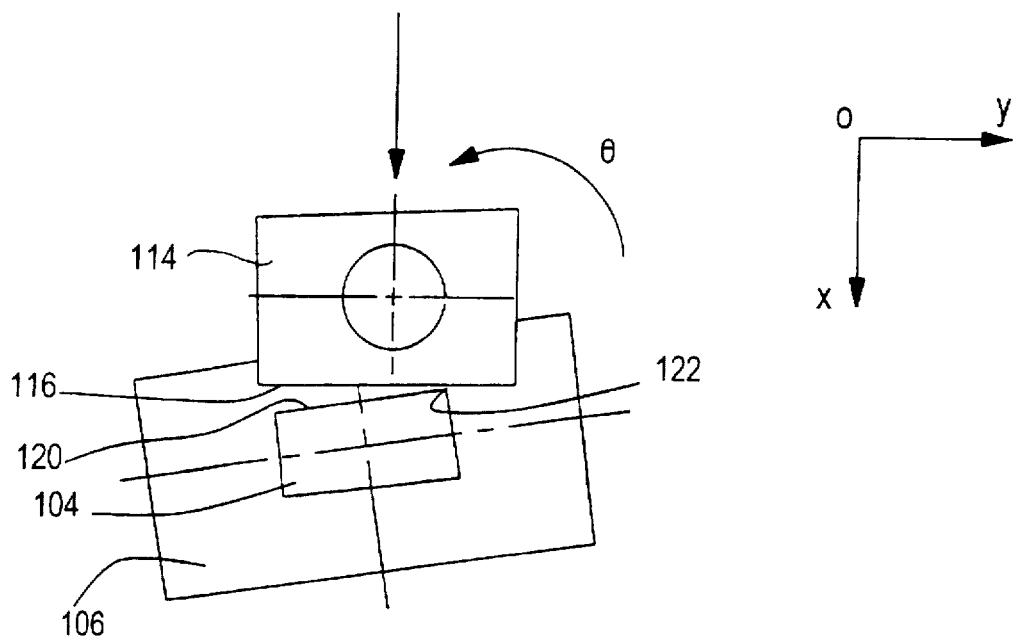
FIG. 6 is a schematic to illustrate for the scenario per FIG. 5 how initial contact between the shear force applying element and the misaligned test specimen generates corrective action prior to application of significant force to the specimen.

FIG. 5 illustrates another circumstance in which there is initial misalignment between the load-applying element 114 and specimen 104. In this scenario, it is the specimen which is mounted with its load-receiving face 120 not quite perpendicular to the direction of relative translational motion between load-applying face 116 and load-receiving face 120. Here, as in the scenario illustrated in FIG. 4, initial contact will occur at 122 as best seen in FIG. 6. As before, rotatable load-applying element 114 will rotate in the direction of the curved arrow, by the necessary angle "θ", so that load-applying face 116 is parallel to and in intimate uniform contact with load-receiving face 120 of specimen 104. Once sufficient relative motion has occurred between load-applying element 114 and specimen 104, and the two load transfer faces 116 and 120 are in intimate parallel contact with each other, further relative motion between the load-applying element 114 and specimen 104 will result in the application of a uniform force on specimen 104. There may, in this particular instance, be a small component of the applied force along the irrotatable load-receiving face 120 of specimen 104.

Test personnel will of course want to avoid mounting the specimen so that such a situation occurs. Hence, first, the probability of it occurring will be very small; and, second, the magnitude of error in mounting the specimen 104 to base 102 in most instances also will be relatively small. Consequently, the force along load-receiving face 120 will itself be very small and the measured applied force will probably be very close to what was intended. Note, however, that there will not be the totally undesirable concentration of applied force on a corner portion of specimen 104 which would at best cause an uneven concentration of stress at the contact point and, in a more extreme situation, may cause physical rupture localized at and about the contact point 122. In other words, the present invention significantly minimizes the probability of improper stress concentration and physical destruction of test specimens at an early and unacceptable stage of the test. This is accomplished easily, inexpensively, and very quickly because it is essentially automatic.

As persons of ordinary skill in the mechanical arts will appreciate, a single base 102 can be adapted so that there may be a plurality of test specimens such as 104 mounted side-by-side so that when base 106 is moved along the y-axis (see FIGS. 3–6) the various test specimens will be sequentially placed in position for the application of the test force by load-applying element 114. This invention, therefore, significantly expedites the testing of plural test specimens, e.g., from a production run, to provide affordable quality control of the bonding of, for example, dies to die pads and the like. Obvious variations on this theme will be readily recognized, and are intended to be comprehended within the invention as broadly disclosed and as claimed in the claims appended below.

Although the present invention has been described and illustrated in detail, it should be clearly understood that the same is by way of illustration and example only and is not to be taken by way of limitation, the spirit and scope of the present invention being limited only by the terms of the appended claims.

What is claimed is:

1. An apparatus for applying a uniform load to an object, comprising:

a loading element mounted to be freely rotatable about a first axis and having a load application surface rotatable at a first radius about the first axis;

first means for holding the object; and second means for controllably moving the loading element relative to the object along a second axis perpendicular to the first axis; and the first and second means cooperating in a first phase in which a load-receiving surface of the object is disposed to make contact with the load application surface of the moving loading element to rotate the loading element about the first axis as needed to ensure that the load application surface is aligned to make uniform contact over a contact area of the load receiving surface and in a second phase in which the uniform contact is maintained while further controlled movement of the loading element relative to the uniformly contacted object applies a uniform load to the object.

2. The apparatus according to claim 1, further comprising:

a third means for adjusting a height of the loading element along the first axis and relative to the object.

3. The apparatus according to claim 1, wherein:

the load application surface is shaped and sized to overlap and extend beyond the contact area at least in the second phase.

4. The apparatus according to claim 2, wherein:

the load application surface is shaped and sized to overlap and extend beyond the contact area at least in the second phase.

5. The apparatus according to claim 1, wherein:

the first means holds the object by an epoxy bond.

6. An apparatus to determine the strength of a bond holding a specimen to a mounting element, comprising:

a bond by which the specimen is bonded to the mounting element;

a loading element movable relative to the specimen in translation along a first axis passing through the specimen and rotatable about a second axis perpendicular to the first axis; and means for moving the loading element along the first axis until contact between the loading element and the specimen causes a rotation of the loading element about the second axis sufficient to ensure uniform contact between the loading element and the specimen.

7. The apparatus according to claim 6, further comprising:

means for determining a load applied by the loading element to the bond via the specimen as the loading element is moved further relative to the specimen while maintaining the uniform contact therewith.

8. A method of applying a uniform force to a test specimen, comprising the step of:

bonding the test specimen to a first element; and obtaining a contact between a rotatably mounted force application element and the bonded test specimen, by relative movement therebetween, to generate an alignment between mutually contacting surfaces of the force application element and the specimen.

9. The method according to claim 8, comprising the further steps of:

providing a movement of the force application element while retaining the alignment, to thereby generate the uniform force on the specimen; and determining a corresponding value of the applied uniform force.

10. The method according to claim 9, comprising the further steps of:

affixing the specimen to a stationary support prior to obtaining the uniform contact between the load application element and the specimen.

11. A method of applying a uniform force to a test specimen, comprising the step of:

obtaining a contact between a rotatable mounted force application element and the test specimen, by relative movement therebetween, to generate an alignment between mutually contacting surfaces of the force application element and the specimen;

providing a movement of the force application element while retaining the alignment, to thereby generate the uniform force on the specimen;

determining a corresponding value of the applied uniform force; and affixing the specimen to a stationary support prior to obtaining the uniform contact between the load application element and the specimen, wherein the affixing step comprises forming a bond by providing an adhesive material between the load application element and the specimen.

12. The method according to claim 11, wherein:

the adhesive material comprises an epoxy component.

13. The method according to claim 11, comprising the further step of:

relating the determined value of the applied uniform force to a shear strength of the bond.

* * * * *